United States Patent
Bosworth et al.

(10) Patent No.: US 11,324,775 B2
(45) Date of Patent: May 10, 2022

(54) COMPOSITIONS AND METHODS FOR THE TREATMENT OF CONTACT LENS DISCOMFORT

(71) Applicant: Azura Ophthalmics Ltd., Tel Aviv (IL)

(72) Inventors: Charles Bosworth, Las Vegas, NV (US); Yair Alster, Tel Aviv (IL); Hila Epstein-Barash, Shoham (IL); Omer Rafaeli, Udim (IL); Marc Gleeson, Longueville (AU)

(73) Assignee: AZURA OPHTHALMICS LTD., Tel Aviv (IL)

( * ) Notice: Subject to any disclaimer, the term of this patent is extended or adjusted under 35 U.S.C. 154(b) by 0 days.

(21) Appl. No.: 17/357,749

(22) Filed: Jun. 24, 2021

(65) Prior Publication Data
US 2021/0315926 A1 Oct. 14, 2021

Related U.S. Application Data

(63) Continuation of application No. PCT/IB2020/000262, filed on Apr. 8, 2020.

(60) Provisional application No. 62/833,281, filed on Apr. 12, 2019.

(51) Int. Cl.
A61K 33/04 (2006.01)
A61P 27/04 (2006.01)
G02C 7/04 (2006.01)

(52) U.S. Cl.
CPC .............. *A61K 33/04* (2013.01); *A61P 27/04* (2018.01); *G02C 7/04* (2013.01)

(58) Field of Classification Search
CPC ............ A61K 33/04; A61P 27/04; G02C 7/04
See application file for complete search history.

(56) References Cited

U.S. PATENT DOCUMENTS

| | | | | |
|---|---|---|---|---|
| 9,463,201 | B2 * | 10/2016 | Alster | A61P 43/00 |
| 10,034,887 | B2 * | 7/2018 | Alster | A61K 8/23 |
| 2007/0104758 | A1 | 5/2007 | Hamilton et al. | |
| 2015/0080349 | A1 | 3/2015 | Blackwell et al. | |
| 2017/0035785 | A1 | 2/2017 | Alster et al. | |
| 2017/0087179 | A1 * | 3/2017 | Amselem | A61K 31/683 |
| 2018/0043024 | A1 | 2/2018 | Sakurai et al. | |
| 2018/0177391 | A1 | 6/2018 | Korb et al. | |
| 2021/0236518 | A1 * | 8/2021 | Alster | A61K 31/122 |

FOREIGN PATENT DOCUMENTS

WO   WO-2020208418 A1   10/2020

OTHER PUBLICATIONS

Tim Willis, et al, Meibomian Gland Function, Lid Wiper Epitheliopathy, and Dry Eye Symptoms, 52 Inv. Ophthalmol. Vis. Sci. 3740 (Year: 2011).*
Jason J. Nichols, et al, Dual-Polymer Drops, Contact Lens Comfort, and Lid Wiper Epitheliopathy, 93 Optom. Vis. Sci. 979 (Year: 2016).*
Nathan Efron, et al, Lid Wiper Epitheliopathy, 53 Prog. Retin. Eye Res., 140 (Year: 2016).*
Robin Chalmers, et al, Cutoff Score and Responsiveness of the 8-Item Contact Lens Dry Eye Questionnaire (CLDEQ-8) in a Large Daily Disposable Contact Lens Registry, 39 Cont. Lens Ant. Eye 342 (Year: 2016).*
Chalmers et al. Contact Lens Dry Eye Questionnaire-8 (CLDEQ-8) and opinion of contact lens performance. Optom Vis Sci. 89:1435-1442 (2012).
Chalmers et al. Contact Lens Dry Eye Questionnaire-8 (CLDEQ-8): Use of an 8-Item Habitual Symptom Score to Reflect Change in Overall Opinion on Contact Lens Performance. Invest Ophthalmol Vis Sci 50:6337 (2009).
Chalmers et al. Cutoff score and responsiveness of the 8-item Contact Lens Dry Eye Questionnaire (CLDEQ-8) in a Large daily disposable contact lens registry. Cont. Lens. Anterior Eye. 39(5):342-52 (2016).
Foulks et al. The TFOS International Workshop on Contact Lens Discomfort: Report of the Subcommittee on Clinical Trial Design and Outcomes. Invest Ophthalmol Vis Sci 54:TFOS157-TFOS182 (2013).
Nelson et al. The International Workshop on Meibomian Gland Dysfunction: Report of the Definition and Classification Subcommittee. Invest Ophthalmol Vis Sci. 52(4):1930-1937 (2011).
Nichols et al. The Performance of the Contact Lens Dry Eye Questionnaire as a Screening Survey for Contact Lens-related Dry Eye. Cornea 21(5):469-475 (2002).
Omali et al. Quantification of individual proteins in silicone hydrogel contact lens deposits. Mol Vis. 19:390-399 (2013).
PCT/IB2020/000262 International Search Report and Written Opinion dated Aug. 12, 2020.
Siddireddy et al. Predictive Potential of Eyelids and Tear Film in Determining Symptoms in Contact Lens Wearers. Optom Vis Sci 95(11):1035-1045 (2018).
Young et al. Soft contact lens-related dryness with and without clinical signs. Optom. Vis. Sci. 89:1125-32 (2012).

* cited by examiner

*Primary Examiner* — Sean M Basquill
(74) *Attorney, Agent, or Firm* — Wilson Sonsini Goodrich & Rosati

(57) ABSTRACT

Described herein are compositions and methods for the treatment of contact lens discomfort (CLD) and/or lid wiper epitheliopathy (LWE). Such compositions comprise keratolytic agents, such as salicylic acid, selenium disulfide, or the like. Topical administration of such compositions to the inner surface of the eyelid provides therapeutic benefit to patients suffering from contact lens discomfort (CLD) and/or lid wiper epitheliopathy (LWE).

20 Claims, 4 Drawing Sheets

SYMPTOM SURVEY

Think about how your eyes have felt in general over the last couple of days. Then, using the scales provided below, please mark a vertical line at the place that best describes your experience with these symptoms:

1. Dryness

None                                                    Maximum

0   —————————————————————  100

2. Grittiness or Scratchiness

None                                                    Maximum

0   —————————————————————  100

3. Soreness or Irritation

None                                                    Maximum

0   —————————————————————  100

4. Burning or Watering

None                                                   Maximum

1. Questions about EYE DISCOMFORT:

a. During a typical day in the past 2 weeks, how often did your eyes feel discomfort while wearing your contact lenses?

0 Never
      1 Rarely
      2 Sometimes
      3 Frequently
      4 Constantly

When your eyes felt discomfort with your contact lenses, how intense was this feeling of discomfort...

b. At the end of your wearing time?

| Never have it | Not at All Intense | | | | Very Intense |
   |---|---|---|---|---|---|
   | 0 | 1 | 2 | 3 | 4 | 5 |

2. Questions about EYE DRYNESS:

a. During a typical day in the past 2 weeks, how often did your eyes feel dry?

0 Never
      1 Rarely
      2 Sometimes
      3 Frequently
      4 Constantly

When your eyes felt dry, how intense was this feeling of dryness...

b. At the end of your wearing time?

| Never have it | Not at All Intense | | | | Very Intense |
   |---|---|---|---|---|---|
   | 0 | 1 | 2 | 3 | 4 | 5 |

*Copyright© Trustees of Indiana University, 1999, all rights reserved*

3. Questions about CHANGEABLE, BLURRY VISION:

a. During a typical day in the past 2 weeks, how often did your vision change between clear and blurry or foggy while wearing your contact lenses?

0 Never
      1 Rarely
      2 Sometimes
      3 Frequently
      4 Constantly

When your vision was blurry, how noticeable was the changeable, blurry, or foggy vision ...

b. At the end of your wearing time?

| Never have it | Not at All Intense | | | | Very Intense |
   |---|---|---|---|---|---|
   | 0 | 1 | 2 | 3 | 4 | 5 |

4. Question about CLOSING YOUR EYES:
   During a typical day in the past 2 weeks, how often did your eyes bother you so much that you wanted to close them?

0 Never
      1 Rarely
      2 Sometimes
      3 Frequently
      4 Constantly

5. Question about REMOVING YOUR LENSES:
   How often during the past 2 weeks, did your eyes *bother you so much* while wearing your contact lenses that you felt as if you needed to stop whatever you were doing and take out your contact lenses?

1 Never
      2 Less than once a week
      3 Weekly
      4 Several times a week
      5 Daily
      6 Several times a day

FIG. 3

COMPOSITIONS AND METHODS FOR THE TREATMENT OF CONTACT LENS DISCOMFORT

CROSS-REFERENCE TO RELATED APPLICATIONS

This application is a continuation of International Application no. PCT/IB2020/000262, filed on Apr. 8, 2020, which claims the benefit of U.S. Provisional Application No. 62/833,281, filed Apr. 12, 2019, which is incorporated herein by reference in its entirety.

BACKGROUND OF THE INVENTION

Contact lens discomfort (CLD) is a condition characterized by episodic or persistent adverse ocular sensations related to lens wear, either with or without visual disturbance, resulting from reduced compatibility between the contact lens and the ocular environment, which can lead to decreased wearing time and discontinuation of contact lens wear. CLD patients present with symptoms of ocular discomfort (e.g., dryness, irritation, discomfort, fatigue, and so forth), these symptoms can increase in severity over the day while the patient is wearing the contact lenses. Symptoms of dryness and discomfort are highly prevalent among contact lens wearers (up to 50%) and are the most commonly cited reason for the discontinuation of contact lens wear with the contact lens dropout rate remaining consistently high (i.e., 16%-34% per year) despite decades of research into contact lens design, materials, rewetting products, and in-use behavior modification(s). CLD is primarily diagnosed by symptomatology as opposed to observation signs. The use of symptoms are thus often used as an outcome measure because they relate directly to the patients' experience with contact lenses and a motivation to seek and use treatment.

Common treatments for CLD include the periodic use of rewetting drops, contact lens removal, contact lens refitting (using different lens designs or materials or replacement schedules), and changes in the contact lens care solutions or regimens, in addition to other less commonly used approaches including topical or systemic medications, alterations in diet, and punctal plugs. Ultimately, CLD is considered as a primary factor associated with permanent discontinuation from contact lens wear.

SUMMARY OF THE INVENTION

With more than 140 million contact lens wearers worldwide, the high prevalence rate for discontinuation represents a significant problem that is, in some instances, a result of ocular tissue changes that occur due to the disruptive presence of any contact lens on the eye. Lid wiper epitheliopathy (LWE) and lid parallel conjunctival folds (LIPCOF) are examples of ocular tissue changes that have been reported as strongly correlated with contact lens wear. LWE is found in 67% to 80% of symptomatic CL wearers, but in only 13% to 32% of asymptomatic subjects. In patients suffering from CLD, it has been verified by histology that cells with atypical keratinization increase in number and extend from the natural stainable line of Marx, where they physiologically occur, over the surface of the lid wiper epithelium.

Many lens related factors have also been associated with CLD including lens material, design, and surface properties. In relation to the surface properties of lenses, changes include biofilm accumulated that can alter the mechanical properties (such as lubricity and wettability) and the interaction between surface deposits and their biological role in maintaining eye health. It has been shown that protein accumulation on the surface of the lens and, in particular, alteration in activity of proteins that, when denatured, lose their natural activity, are associated with CLD. Thus, in some instances, providing an on-eye therapeutic agent that is able to treat CLD and/or LWE or one or more symptoms thereof can protect against the accumulation of some proteins and/or lipids and/or mucins and prevent the denaturation of proteins. In particular there has been evidence of accumulation of keratin on contact lenses during wear and this has been strongly correlated with symptoms of dryness (Negar Babaei Omali et al. Mol Vis. 2013; 19: 390-399).

The present disclosure provides methods of treating contact lens discomfort (CLD) and/or lid wiper epitheliopathy (LWE), such as by administering a keratolytic agent to the eye (or surrounding tissue, such as to the eyelid (e.g., eyelid margin)) of an individual in need thereof. In some embodiments, treatment of the contact lens discomfort comprises treating one or more symptoms associated with contact lens discomfort (e.g., as described herein). In specific embodiments, a symptom associated with contact lens discomfort is a symptom identifiable by the individual and/or by a clinician.

In certain embodiments, a method provided herein is associated with treating any symptom associated with contact lens discomfort, such as, by way of non-limiting example, inflammation, dryness, pain, or a combination thereof.

In specific embodiments, a composition used in a method provided herein comprises a keratolytic agent selected from the group consisting of benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic Acid, and sulfanegen. In specific embodiments, a composition used in a method provided herein comprises a keratolytic agent selected from the group consisting of benzoyl peroxide, coal tar, dithranol, salicylic acid, selenium disulfide, alpha-hydroxy acid, urea, lactic acid, sodium thioglycolate, zinc pyrithione, and zinc L-pyrrolidone carboxylate.

In some embodiments, provided herein is a method for treating contact lens discomfort (CLD), symptoms thereof (e.g., signs associated with symptoms thereof), in an individual in need thereof. In certain embodiments, the method comprises topically administering to an eye (or surrounding tissue, such as to the eyelid (e.g., eyelid margin)) of the individual a pharmaceutically acceptable composition, the composition comprising a therapeutically-effective amount of at least one keratolytic agent (e.g., as described herein). In specific embodiments, the pharmaceutically acceptable composition further comprises an ophthalmically-acceptable carrier (e.g., comprising an ophthalmically-acceptable vehicle and/or ophthalmically-acceptable excipient). In certain specific embodiments, the pharmaceutically acceptable composition consists essentially of the at least one keratolytic agent and the ophthalmically-acceptable carrier. In certain specific embodiments, the pharmaceutically acceptable composition consists of the at least one keratolytic agent and the ophthalmically-acceptable carrier.

In certain embodiments, administration (e.g., topical administration) (e.g., in any method described herein) to the eye of an individual comprises topical ocular administration, (e.g., topical) palpebra (lid) administration (e.g., to the inside and/or outside of the lid), or a combination thereof. In some embodiments, administration (e.g., topical administration) (e.g., in any method described herein) to the eye of an individual comprises administration to an eyelid margin of the eye. In certain preferred embodiments, (e.g., direct) administration is (e.g., topical) administration to the inner lid surface. In more preferred embodiments, administration is or comprises (e.g., direct) administration to the lid wiper region of the inner lid surface. In certain embodiments, administration is or comprises (e.g., direct) administration to the lid wiper region and the stratified squamous epithelium region and/or the subtarsal fold region of the lid. In some embodiments, administration is or comprises (e.g., direct) administration to the lid wiper region, the stratified squamous epithelium region and the subtarsal fold region of the lid. In certain embodiments, administration is or comprises (e.g., direct) administration to the lid wiper, the stratified squamous epithelium, the subtarsal fold, and the stratified columnar epithelium regions of the lid. In certain specific embodiments, topical administration to the eye of the individual comprises direct topical administration to (at least a portion of) a palpebra conjuctiva (or inner surface of an eyelid) of the eye. In some embodiments, topical administration to the eye comprises topical administration that results in delivery (following administration) of the composition, or at least a portion of the keratolytic agent thereof, to (at least a portion of) the palpebra conjuctiva (or inner surface of an eyelid) of the eye. In some embodiments, the composition is administered (e.g., in any method described herein) to a single eye of an individual. In other embodiments, the composition is administered (e.g., in any method described herein) to two eyes of an individual (e.g., at the same or different times, by the same or a different person, and in the same or different concentrations or amounts).

In some embodiments, the contact lens discomfort and/or lens wiper epitheliopathy described herein and/or treated according to any method herein is associated with a (e.g., clinically identified or suspected) alteration to a portion of an eye, such as one or more eyelid(s) (e.g., inner surface thereof, such as the palpebra conjunctiva, or any other portion thereof, such as the lid wiper region and/or lid parallel conjunctival folds). In specific embodiments, an alteration to the inner surface of the eyelid (or palpebra conjunctiva) is to the leading edge of the palpebra conjunctiva (e.g., the "lid wiper" region of the lid). In certain embodiments, a process provided herein comprises identifying an alteration in the inner surface of the lid (e.g., lid wiper region or palpebra conjunctiva), or leading edge thereof, of the individual (e.g., in a clinical setting, such as prior to administration of the pharmaceutical composition thereto) or administering the composition to an individual for whom an alteration in the inner surface of the lid (e.g., lid wiper region or palpebra conjunctiva) has been identified. In various instances, any alteration (e.g., problematic alteration, or alteration corresponding to contact lens discomfort (CLD)) of the inner surface of the lid (e.g., lid wiper region or palpebra conjunctiva) is present and/or targeted, such as trauma to the inner surface of the lid (e.g., lid wiper region or palpebra conjunctiva), or alterations resulting from trauma (e.g., wherein the trauma is associated with friction between the inner surface of the lid (e.g., the palpebra conjuctiva) and the lens). In some embodiments, the alteration is or comprises (e.g., atypical) keratinization (e.g., para-keratinization (pk)) of the alteration in a portion of the inner surface of the lid (e.g., in a portion of the lid wiper region or palpebra conjunctiva).

In specific embodiments, the contact lens discomfort and/or lens wiper epitheliopathy described herein and/or treated according to any method herein is associated with a (e.g., clinically identified or suspected) alteration in the inner surface of the lid (e.g., lid wiper region or palpebra conjunctiva) of the upper eyelid. In other specific embodiments, the contact lens discomfort treated according to any method herein is associated with a (e.g., clinically identified or suspected) alteration to the inner surface of the lid (e.g., lid wiper region or palpebra conjunctiva) of the lower eyelid.

Also provided in certain embodiments herein are methods of treating lid wiper epitheliopathy (LWE), such as by administering a keratolytic agent to the eye or surrounding tissue, such as to the eyelid or portion thereof (e.g., eyelid margin) of an individual in need thereof. In some embodiments, treatment of the lid wiper epitheliopathy (LWE) comprises treating symptoms associated with lid wiper epitheliopathy (LWE). In specific embodiments, the symptom associated with lid wiper epitheliopathy (LWE) is a symptom identifiable by the individual and/or by a clinician. In certain embodiments, a method provided herein is associated with treating any symptom associated with lid wiper epitheliopathy (LWE), such as, by way of non-limiting example, inflammation, dryness, pain, or a combination thereof. In specific embodiments, the keratolytic agent is selected from the group consisting of benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic acid, and sulfanegen. In specific embodiments, the keratolytic agent is selected from the group consisting of benzoyl peroxide, coal tar, dithranol, salicylic acid, selenium disulfide, alpha-hydroxy acid, urea, lactic acid, sodium thioglycolate, zinc pyrithione, and zinc L-pyrrolidone carboxylate.

In some embodiments, provided herein is a method for treating lid wiper epitheliopathy (LWE), symptoms thereof (e.g., signs associated with symptoms thereof), in an individual in need thereof. In certain embodiments, the method comprises topically administering to an eye (or surrounding tissue thereof, such as to the eyelid or portion thereof (e.g., eyelid margin)) of the individual a pharmaceutically acceptable composition, the composition comprising a therapeutically-effective amount of at least one keratolytic agent. In specific embodiments, the pharmaceutically acceptable composition further comprises an ophthalmically-acceptable carrier (e.g., comprising an ophthalmically vehicle and an isotonic agent). In certain embodiments, topical administration to the eye of the individual comprises topical ocular administration, topical palpebra (lid) administration (e.g., to the inside and/or outside of the lid), or a combination thereof. In some embodiments, topical administration to the eye or eyelid of the individual comprises administration to an eyelid margin of the eye of the individual. In specific embodiments, topical administration to the eye of the individual comprises direct topical administration to (at least a portion of) the lid wiper region of one or more lid(s) (of the eye). In some embodiments, topical administration to the eye comprises topical administration that results from delivery (following administration) of the composition, or at least portion of the keratolytic agent thereof, to (at least a portion of) a palpebra conjuctiva (or lid wiper region) of the eye.

In certain preferred embodiments, (e.g., direct) administration is (e.g., topical) administration to the inner lid surface. In more preferred embodiments, administration is or comprises (e.g., direct) administration to the lid wiper region of the inner lid surface. In certain embodiments, administration is or comprises (e.g., direct) administration to the lid wiper region and the stratified squamous epithelium region and/or the subtarsal fold region of the lid. In some embodiments, administration is or comprises (e.g., direct) administration to the lid wiper region, the stratified squamous epithelium region and the subtarsal fold region of the lid. In certain embodiments, administration is or comprises (e.g., direct) administration to the lid wiper, the stratified squamous epithelium, the subtarsal fold, and the stratified columnar epithelium regions of the lid.

In certain embodiments, the lid wiper epitheliopathy (LWE) is upper lid wiper epitheliopathy (LWE). In some embodiments, however, the lid wiper epitheliopathy (LWE) is lower lid wiper epitheliopathy (LWE).

In some embodiments, the individual (e.g., patient) being treated according to a method described herein wears one or more contact lenses (e.g., on a regular basis, such as for one or more hours per day or one or more days per week). In some embodiments, the individual being treated according to a method described herein wears one or more contact lenses two or more days per week, such as three, four, five, six, or seven days per week. In some embodiments, the individual being treated according to a method described herein wears one or more contact lenses for the duration of treatment (e.g., as described herein). In other embodiments, the individual being treated according to a method described herein does not wear one or more contact lenses for the duration of treatment (e.g., regular wear is resumed following a prescribed treatment course). In certain embodiments, the lid wiper epitheliopathy is associated with contact lens discomfort (CLD) and/or the individual suffers from, is diagnosed with suffering from, or is suspected of suffering from contact lens discomfort (CLD). In some instances, contact lens discomfort is primarily associated with the upper lid because of the increase interaction of the upper lid wiper with the contact lens relative to the interaction of the lower lid wiper with the contact lens (e.g., due to the longer motions of the upper lid when blinking).

In certain embodiments, any method provided herein (e.g., in treating contact lens discomfort (CLD) and/or in treating lid wiper epitheliopathy (LWE)), the individual suffers from, has been diagnosed with, or is suspected of suffering from any severity of lid wiper epitheliopathy (LWE). For example, in some embodiments, the lid wiper epitheliopathy is clinically graded as having a severity level of 1 (e.g., on a discrete 0 to 3 scale or a 0 to 3 subjective scale, with a 3 being the most severe and 0 being free of the disorder). In some embodiments, the lid wiper epitheliopathy is clinically graded as having a severity level of at least 1 (e.g., on a discrete 0 to 3 scale or a 0 to 3 subjective scale, with a 3 being the most severe and 0 being free of the disorder), such as at least 2. In certain embodiments, the lid wiper epitheliopathy is clinically graded as having a severity level of 2. In certain embodiments, the lid wiper epitheliopathy is clinically graded as having a severity level of 3.

In some embodiments, the lid wiper epitheliopathy presents in any manner, such as a clinically significant manner. In certain embodiments, the lid wiper epitheliopathy comprises and/or is indicated by the presence of trauma to and/or around the lid wiper region of the eyelid (e.g., upper lid). In some embodiments, treatment is continued until a reduction in such trauma is observed. In certain embodiments, the lid wiper epitheliopathy comprises and/or is indicated by the presence of (e.g., atypical) keratinization (e.g., para-keratinization (pk)) of and/or around the lid wiper region of the eyelid (e.g., upper lid). In some embodiments, treatment is continued until a reduction in such (e.g., atypical) keratinization (e.g., para-keratinization (pk)) is observed. In certain embodiments, the lid wiper epitheliopathy comprises and/or is indicated by the presence of inflammation of and/or around the lid wiper region of the eyelid (e.g., upper lid). In some embodiments, treatment is continued until a reduction in such inflammation is observed. In certain embodiments, the lid wiper epitheliopathy comprises and/or is indicated by the presence of dryness of the eye. In some embodiments, treatment is continued until a reduction in such dryness is observed. In certain instances, such conditions are considered present when they are present in all or part of the indicated region of the eye.

Provided in certain embodiments herein are methods of treating eye dryness, such as by administering a keratolytic agent to the eye of an individual in need thereof. In some embodiments, the dryness is associated with contact lens discomfort (CLD) and/or lid wiper epitheliopathy (LWE). In various embodiments herein, such therapies are as described herein for any method involving the treatment of contact lens discomfort (CLD) and/or lid wiper epitheliopathy (LWE).

Provided in certain embodiments herein are methods of treating eye pain, such as by administering a keratolytic agent to the eye of an individual in need thereof. In some embodiments, the pain is associated with contact lens discomfort (CLD) and/or lid wiper epitheliopathy (LWE). In various embodiments herein, such therapies are as described herein for any method involving the treatment of contact lens discomfort (CLD) and/or lid wiper epitheliopathy (LWE).

Provided in certain embodiments herein are methods of treating eye inflammation, such as by administering a keratolytic agent to the eye of an individual in need thereof. In some embodiments, the inflammation is associated with contact lens discomfort (CLD) and/or lid wiper epitheliopathy (LWE). In various embodiments herein, such therapies are as described herein for any method involving the treatment of contact lens discomfort (CLD) and/or lid wiper epitheliopathy (LWE).

Provided in certain embodiments herein are methods of inhibiting alteration of a contact lens, or surface thereof, in the eye of an individual. In specific embodiments, such methods comprise (e.g., topically) administering to an eye or an eyelid associated with or a contact lens in contact with the eye a pharmaceutically acceptable composition. In certain embodiments, the pharmaceutically acceptable composition comprising a therapeutically-effective amount of at least one keratolytic agent and an ophthalmically-acceptable carrier.

In certain specific embodiments, the method is a method for maintaining (e.g., preventing alteration of) or altering one or more surface properties (e.g., smoothness, lack of biofilm, etc.) of a contact lens (e.g., in an eye of an individual). In certain embodiments, the individual suffers from contact lens discomfort (CLD) and/or lid wiper epitheliopathy (LWE). In some instances, by inhibiting alteration of a contact lens in an individual wearing such contact lens, the method inhibits the development and/or reduces the severity of contact lens discomfort (CLD) and/or lid wiper epitheliopathy (LWE) in the individual. In some embodiments, the method for maintaining (e.g., preventing alteration of) or altering one or more surface properties (e.g., smoothness, lack of biofilm, etc.) of a contact lens comprises administering a composition (e.g., as described herein) to the contact lens. In other embodiments, the method for maintaining (e.g., preventing alteration of) or altering one or more surface properties (e.g., smoothness, lack of biofilm, etc.) of a contact lens comprises administering a composition (e.g., as described herein) to the eye or surrounding tissue (e.g., eyelid or portion thereof (e.g., eyelid margin)) associated with the contact lens.

In certain specific embodiments, provided herein is a method of inhibiting biofilm formation on a contact lens in the eye of an individual, the method comprising topically administering to an eye or surrounding tissue (e.g., an eyelid (e.g., eyelid margin)) associated with the contact lens or to the contact lens in contact with the eye a pharmaceutically acceptable composition. In some embodiments, the pharmaceutically acceptable composition comprising a therapeutically-effective amount of at least one keratolytic agent (e.g., as described herein) and an ophthalmically-acceptable carrier.

In certain embodiments, an individual treated according to any method provided herein has been assessed using a symptom scoring technique, such as a symptom scoring technique suitable for diagnosing contact lens discomfort (CLD), lid wiper epitheliopathy (LWE), eye dryness, eye pain, eye inflammation, or any other indication described herein. In specific embodiments, the individual has been diagnosed using a contact lens dry eye questionnaire (CLDEQ) measurement tool (e.g., as described by Nichols et al. *The Performance of the Contact Lens Dry Eye Questionnaire as a Screening Survey for Contact Lens-related Dry Eye, Cornea* 2002; 21(5): 469-475, which is incorporated herein by reference for such disclosures), such as the CLDEQ-8 measurement tool (e.g., as described by Chalmers et al, *Contact Lens Dry Eye Questionnaire-8 (CLDEQ-8) and opinion of contact lens performance. Optom Vis Sci.* 2012; 89: 1435-1442 or as copyrighted by Indiana University, both of which are incorporated herein by reference for such disclosures), or any part or portion thereof. In specific embodiments, the individual has a CLDEQ-8 score of at least 5. In some specific embodiments, the individual has a CLDEQ-8 score of at least 10. In more specific embodiments, the individual has a CLDEQ-8 score of at least 12. In still more specific embodiments, the individual has a CLDEQ-8 score of at least 15. In yet more specific embodiments, the individual has a CLDEQ-8 score of at least 18. In some embodiments, a method provides improvement in the CLDEQ-8 measurement tool. In certain embodiments, an individual treated according to any method provided herein is or has been assessed for comfortable wear time and/or subjective vision assessment prior to administration (e.g., using VAS as outcome variables). In some embodiments, a method provides improvement in comfortable wear time and/or subjective vision assessment. In various embodiments, any other suitable symptom scoring process (e.g., scoring negative effects of the disorder and/or signs of symptoms of the disorder) is optionally utilized to diagnose an individual in need of a therapy described herein (e.g., diagnosing the individual as suffering from LWE or CLD, thereby) (such as, e.g., any of the symptoms (e.g., symptom signs) or combination thereof described in Siddireddy, et al, *Predictive Potential of Eyelids and Tear Film in Determining Symptoms in Contact Lens Wearers. Optom Vis Sci* 2018; 95(11): 1035-1045, which is incorporated herein by reference for such disclosures).

In some embodiments, an individual treated according to any method provided herein has not been diagnosed with meibomian gland dysfunction (MGD). In some embodiments, an individual being treated for CLD as provided herein has not been diagnosed with MGD. In some embodiments, an individual being treated for CLD as provided herein does not suffer from MGD. It is noted that according to Foulks et al. *The TFOS International Workshop on Contact Lens Discomfort: Report of the Subcommittee on Clinical Trial Design and Outcomes. Invest Ophthalmol Vis Sci.* 2013; 54: TFOS157-TFOS182, that the combined results of studies with the primary objective of predicting CLD suggest that the clinical outcome variables of tear stability, tear meniscus height/area, "lid wiper epitheliopathy" (LWE), and lid parallel conjunctival folds (LIPCOF) are most likely to be predictive of CLD. Notably absent from this finding are traditional measures of MGD such as gland grading (e.g., Meibomian Gland Score (MGS)). In fact, Young et al., *Soft contact lens-related dryness with and without clinical signs. Optom. Vis. Sci.* 2012; 89:1125-32, reported that 23% of symptomatic soft contact lens wearers who reported significant soft contact lens-related dryness using the CLDEQ were without signs of disease.

In some embodiments, an individual treated according to any method provided herein provides or is continued until the method provides a reduction in a composite scale for symptoms (e.g., such symptoms including, e.g., dryness, grittiness, scratchiness, soreness, irritation, burning, watering, or any combination of two or more thereof). In specific embodiments, the method provides an improvement in horizontal (width) and/or sagittal (height) lesions (e.g., of the lid wiper). In certain embodiments, the method provides an improvement in lid parallel conjunctival folds (LIPCOF). In certain embodiments, the method provides improvements in eyelid signs of contact lens discomfort (CLD). In certain embodiments, the method provides improvements in the tear film signs of compact lens discomfort (CLD). In some embodiments, the method provides improvements in meibomian gland secretion (MGS) and/or meibomian glands yielding lipid secretion (MGYLS).

As such, described herein, are methods and formulations for treating various ocular disorders (e.g., contact lens discomfort (CLD) and/or lid wiper epitheliopathy (LWE)) using a keratolytic agent. In specific embodiments, the keratolytic agent is selected from the group consisting of benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic Acid, and sulfanegen. In some embodiments, the keratolytic agent is selected from the group consisting of benzoyl peroxide, coal tar, dithranol, salicylic acid, selenium disulfide, alpha-hydroxy acid, urea, lactic acid, sodium thioglycolate, zinc pyrithione, and zinc L-pyrrolidone carboxylate. In some embodiments, the keratolytic agent is salicylic acid or selenium disulfide. In some embodiments, the keratolytic agent is selenium disulfide. In some embodiments, the concentration of the selenium disulfide in the composition is between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein). In some embodiments, the concentration of the selenium disulfide in the composition is at least about 0.01%, such as at least about 0.05%, about 0.1%, about 1%, about 2%, about 2.5%, about 5%, about 10%, or more. In some embodiments, the concentration of the selenium disulfide in the composition is no more than about 10%, such as no more than about 5%, about 2.5%, about 2%, about 1%, about 0.5%, about 0.1%, or less. In some embodiments, the keratolytic agent is salicylic acid. In some embodiments, the concentration of the salicylic acid in the composition is between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein). In some embodiments, the concentration of the salicylic acid in the composition is at least about 0.01%, such as at least about 0.05%, about 0.1%, about 1%, about 2%, about 2.5%, about 5%, about 10%, or more. In some embodiments, the concentration of the salicylic acid in the composition is no more than about 10%, such as no more than about 5%, about 2.5%, about 2%, about 1%, about 0.5%, about 0.1%, or less. In some embodiments, the composition is topically administered to the individual until the target disorder and/or a symptom (e.g., sign of a symptom) associated therewith is relieved (e.g., partially or completely). In some embodiments, the composition is topically administered to the patient periodically after relief is achieved. In some embodiments, the topical administration is a single administration (e.g., the composition is administered a single time). In some embodiments, the topical administration is a periodic administration (e.g., the composition is administered periodically, such as once per day, twice per day, once per week, twice per week, biweekly, etc.). In some embodiments, the periodic administration is once per day (e.g., the composition is administered once per day). In some embodiments, periodic administration is two times per day (e.g., the composition is administered at least two times per day). In some embodiments, periodic administration is two times per week (e.g., the composition is administered at least two times per week). In some embodiments, the composition for topical administration is a semi-solid composition. In some embodiments, the composition for topical administration is homogenous. In some embodiments, the composition for topical administration is a dispersion or suspension. In some embodiments, the composition for topical administration is hydrophilic. In some embodiments, the composition for topical administration is hydrophobic. In some embodiments, the composition for topical administration comprises an oleaginous base. In some embodiments, the ophthalmically-acceptable carrier comprises at least one ophthalmically-acceptable excipient. In certain embodiments, the composition for topical administration is a gel, such as a non-aqueous gel. In other embodiments, the composition is a suspension, dispersion, hydrophobic oil, foam, liposome, emulsion, lotion, microparticle, or other suitable formulation.

In one embodiment, topically administration of a composition provided herein to the individual is such that the composition reaches the eyelid margin of the patient. In specific embodiments, the composition comprises a therapeutically-effective amount of a keratolytic agent in an ophthalmically-acceptable carrier. In some embodiments, the keratolytic agent is salicylic acid or selenium disulfide. In some embodiments, the keratolytic agent is selenium disulfide. In some embodiments, the concentration of the selenium disulfide in the composition is between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein). In some embodiments, the concentration of the selenium disulfide in the composition is at least about 0.01%, such as at least about 0.05%, about 0.1%, about 1%, about 2%, about 2.5%, about 5%, about 10%, or more. In some embodiments, the concentration of the selenium disulfide in the composition is no more than about 10%, such as no more than about 5%, about 2.5%, about 2%, about 1%, about 0.5%, about 0.1%, or less. In some embodiments, the composition for topical administration is homogenous. In some embodiments, the composition for topical administration is a dispersion or suspension. In some embodiments, the composition for topical administration is hydrophilic. In some embodiments, the composition for topical administration comprises an oleaginous base. In some embodiments, the ophthalmically-acceptable carrier comprises at least one ophthalmically-acceptable excipient. In certain embodiments, the composition for topical administration is a gel, such as a non-aqueous gel. In other embodiments, the composition is a suspension, dispersion, hydrophobic oil, foam, liposome, emulsion, lotion, microparticle, or other suitable formulation.

In one aspect, the methods and formulations described herein include (e.g., additional) pharmacological agents that are useful for the treatment of ocular disorders, such as dry eye, eye pain, eye inflammation, contact lens discomfort (CLD), and/or lid wiper epitheliopathy (LWE), in a subject in need. In some embodiments, the formulations described herein are applied to an eye of a patient in need. In some embodiments, the formulations described herein are applied to an eyelid (e.g., eyelid margin) of a patient in need. In some embodiments, the formulations described herein are applied to a palpebra conjunctiva of a patient in need. In some embodiments, a formulation described here is applied to a single eye or tissue surrounding the eye (e.g., eyelid (e.g., eyelid margin or palpebra conjunctiva) of a patient in need. In some embodiments, a formulation described here is applied to a two eyes or tissue surrounding two eyes (e.g., eyelid (e.g., eyelid margin or palpebra conjunctiva) of a patient in need. In some embodiments, multiple applications of the formulations are required (e.g., periodic applications, such as daily, twice-daily, weekly, twice weekly, or biweekly applications).

In some embodiments, in any of the methods provided herein, the method further comprises performing a physical intervention such as application of a warm compress, debridement, therapeutic expression, or a combination thereof (e.g., debridement coupled with therapeutic expression) in an eye of the individual. In certain embodiments, debridement is performed in one eye and debridement coupled with therapeutic expression is performed in another eye. In some embodiments, a physical intervention is performed after administration of a composition provided herein. For example, in some embodiments, the physical intervention is performed at least about 5 minutes after administration of the composition, such as at least about 10 minutes, about 20 minutes, about 30 minutes, about 1 hour, about 2, hours, about 4 hours, about 8 hours, about 12 hours, about 24 hours, about 48 hours, about 72 hours, about 1 week, about 2 weeks, about 3 weeks, about 4 weeks, about 1 month, or longer after administration of a composition provided herein. In some embodiments, the composition is administered periodically and the physical intervention is performed a single time, such as about 1 month after an initial administration of the composition.

In some embodiments, during administration the eye globe ("eyeball") is shielded, at least in part, to prevent or inhibit the pharmacological agents from contacting the eye globe of the individual. Further described are kits comprising a formulation described herein along with a device that shields the eye from contact with the formulation.

The methods and formulations described herein include an active agent at a therapeutic level, that by itself, or in combination with other components, acts to provide a therapeutic benefit, such as treating a disorder described herein or a symptom associated therewith. Further, in some embodiments, the active agent is formulated or applied, such that it is acceptable to the surface of the eye (e.g., not causing undue irritation or disruption to the epithelial surface of the eye). In certain embodiments, the active agent is formulated and/or applied such that lipid producing cells are not compromised (e.g., when put into contact with the formulation).

In some embodiments, the formulation is applied for a duration and frequency that is acceptable and practical to the physician or patient administering the agent. For example, a physician applies a formulation described herein weekly or twice a week for several weeks to induce opening (at least in part) of the obstruction and the patient applies a different formulation on a daily basis, or the patient uses a more potent formulation on a daily basis for several weeks and then, subsequently uses a less potent formulation of a daily basis thereafter.

In some embodiments the method of application varies, depending on the concentration of the active agent and/or the severity of the ocular disorder or symptom treated, including but not limited to shielding the ocular surface. In other embodiments, the method of application or formulation (e.g., with or without preservatives such as benzalkonium chloride (BAK)), is varied to enhance the penetration or residency time on the target tissue to enhance the treatment effect. In other embodiments, the method of application or formulation, is varied to enhance the penetration or residency time on the target tissue to minimize the amount of time necessary. In other embodiments, the method of application or formulation, is formulated (e.g., with viscosity enhancing agent and/or skin-adhesive agent) to increase contact with the target tissue while minimizing contact with non-target tissues, including the eye, and thus limit or reduce any undesired collateral activity.

In certain aspects of the methods and formulations described herein, the concentration of the active agent, and the components of co-formulation are optimized to deliver the minimum effective concentration of active agent to achieve the therapeutic benefit while minimizing any ocular irritation or disruption, or irritation or disruption to surrounding ocular tissues.

In some embodiments, the active pharmacological agent is a keratolytic and/or keratoplastic agent chosen from benzoyl peroxide, coal tar, dithranol, salicylic acid, selenium disulfide, inorganic selenium compounds such as selenium disulfide, $SeCl_4$, $Na_2SeO_3$, organo-selenium compounds such as Ebselen (2-phenyl-1, 2-benzisoselenazol-3(2H)-one) or its analogues, alpha-hydroxy acid, urea, lactic acid or sodium thioglycolate. In some embodiments, the active pharmacological agent is a keratolytic and/or keratoplastic agent chosen from benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic Acid, and sulfanegen. In some embodiments, the keratolytic and/or keratoplastic agent is chosen from benzoyl peroxide, coal tar, dithranol, salicylic acid or selenium disulfide. In some embodiments, the keratolytic and/or keratoplastic agent is salicylic acid or selenium disulfide. In some embodiments, the keratolytic and/or keratoplastic agent is salicylic acid. In some embodiments, the keratolytic and/or keratoplastic agent is selenium disulfide. In some embodiments, the at least one keratolytic and/or keratoplastic agent is salicylic acid. In some embodiments, the at least one keratolytic and/or keratoplastic agent is selenium disulfide. In some embodiments, the concentration of the salicylic acid in the composition is between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein). In some embodiments, the concentration of the salicylic acid in the composition is at least about 0.01%, such as at least about 0.05%, about 0.1%, about 1%, about 2%, about 2.5%, about 5%, about 10%, or more. In some embodiments, the concentration of the salicylic acid in the composition is no more than about 10%, such as no more than about 5%, about 2.5%, about 2%, about 1%, about 0.5%, about 0.1%, or less. In some embodiments, the concentration of the selenium disulfide in the composition is between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein). In some embodiments, the concentration of the selenium disulfide in the composition is at least about 0.01%, such as at least about 0.05%, about 0.1%, about 1%, about 2%, about 2.5%, about 5%, about 10%, or more. In some embodiments, the concentration of the selenium disulfide in the composition is no more than about 10%, such as no more than about 5%, about 2.5%, about 2%, about 1%, about 0.5%, about 0.1%, or less.

In certain embodiments, a symptom associated with CLD or LWE treated according to a method provided herein comprises a symptom (e.g., a departure from normal function or feeling which is apparent to an individual or patient, reflecting the presence of an unnatural state or of a disease or disorder; a symptom may be objective or subjective). In certain embodiments, a symptom associated with CLD or LWE described herein includes any one or more of dryness, grittiness, scratchiness, soreness, irritation, burning, and/or watering in the eye or tissue surrounding the eye (e.g., of an individual or patient who wears or is wearing at least one contact lens and/or is suffering from or suspected of suffering from CLD or LWE). In certain embodiments, such a symptom is shortened time of contact lens wear. In some embodiments, the presence of one or more such symptom(s) is utilized to diagnose an individual or patient as suffering from CLD or LWE.

In some embodiments, other symptoms or signs are present in an individual suffering from CLD and/or LWE, or are utilized to diagnose an individual as suffering from CLD and/or LWE. In some embodiments, such symptoms or signs include abnormal lid-parallel conjunctival folds, meibomian foam, tear evaporation rate (with or without contact lens), palpebral roughness, palpebral staining, palpebral hyperemia, or a combination of one or more such symptoms or signs.

BRIEF DESCRIPTION OF THE DRAWINGS

FIG. 2 shows the Visual Analog Scale (VAS) sensitive to CLD.

FIG. 3 shows the Contact Lens Dry Eye Questionnaire-8 (CLDEQ-8).

DETAILED DESCRIPTION OF THE INVENTION

Figure 1:
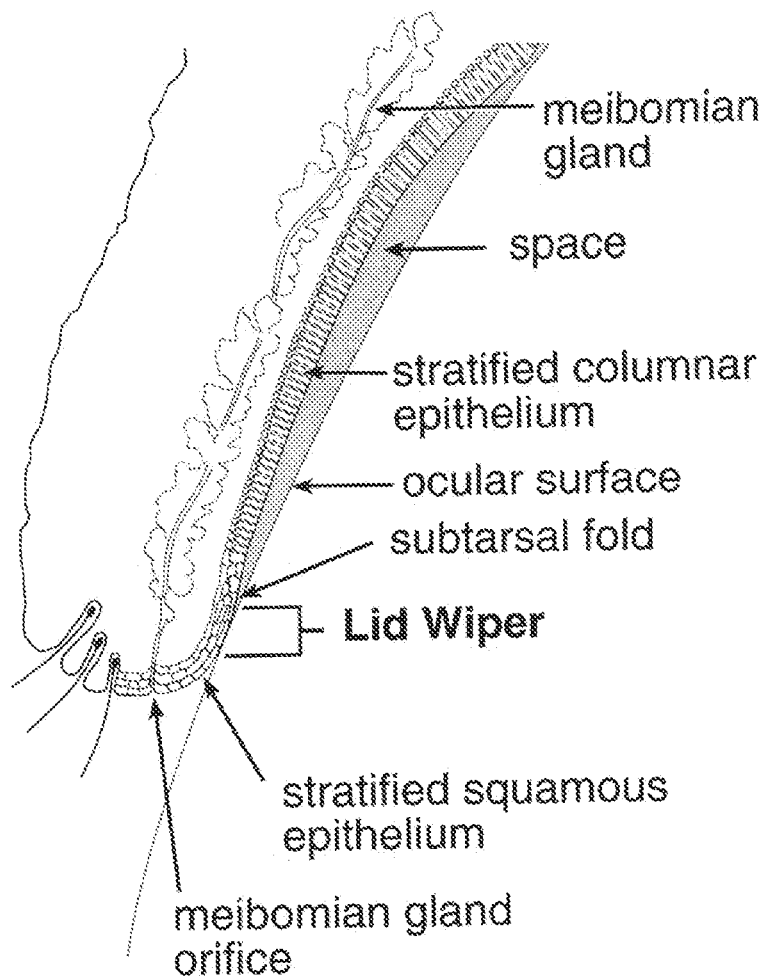
FIG. 1 illustrates a cross-sectional schematic of an exemplary normally functioning eyelid in relation to an ocular surface.

Provided in a variety of embodiments herein are method of treating ocular disorders and symptoms thereof by administering a therapeutically effective amount of a pharmacologically active agent provided herein to an eye (e.g., globe or lid) of an individual in need thereof. In specific embodiments, the methods comprise treating contact lens discomfort (CLD) or symptoms thereof. In certain specific embodiments, the methods comprise treating lid wiper epitheliopathy (LWE) or symptoms thereof. In certain embodiments, the method comprises treating dry eye, eye pain, eye inflammation, or any other disorder or symptom described herein, such as wherein such a disorder or symptom is associated with contact lens discomfort (CLD) or lid wiper epitheliopathy (LWE). In specific embodiments, the methods comprise administering a composition to a contact lens configured to be used on an eye of an individual (e.g., patient) (e.g., to prevent alterations to a surface of the contact lens [e.g., to preserve smoothness and/or reduce biofilm formation] and/or to regulate the accumulation of protein [e.g., keratin] and/or lipids, mucins, and denatured proteins which have been associated with CLD on the contact lens).

Provided in certain embodiments herein are methods of treating contact lens discomfort (CLD), such as by administering a keratolytic agent to the eye or its surrounding tissue (e.g., eyelid (e.g., eyelid margin)) of an individual in need thereof. In some embodiments, treatment of the contact lens discomfort comprises treating one or more symptoms associated with contact lens discomfort. In specific embodiments, a symptom associated with contact lens discomfort is a symptom identifiable by the individual and/or by a clinician. In certain embodiments, a method provided herein is associated with treating any symptom associated with contact lens discomfort, such as, by way of non-limiting example, inflammation, dryness, pain, or a combination thereof. In specific embodiments, the keratolytic agent is selected from the group consisting of benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic acid, and sulfanegen. In specific embodiments, the keratolytic agent is benzoyl peroxide, coal tar, dithranol, salicylic acid, selenium disulfide, alpha-hydroxy acid, urea, lactic acid, sodium thioglycolate, zinc pyrithione, or zinc L-pyrrolidone carboxylate.

Also provided in certain embodiments herein are methods of treating lid wiper epitheliopathy (LWE), such as by administering a keratolytic agent to the eye or its surrounding tissue (e.g., eyelid (e.g., eyelid margin) or palpebra conjunctiva) of an individual in need thereof. In some embodiments, treatment of the lid wiper epitheliopathy (LWE) comprises treating symptoms associated with lid wiper epitheliopathy (LWE). In specific embodiments, the symptom associated with lid wiper epitheliopathy (LWE) is a symptom identifiable by the individual and/or by a clinician. In certain embodiments, a method provided herein is associated with treating any symptom associated with lid wiper epitheliopathy (LWE), such as, by way of non-limiting example, inflammation, dryness, pain, or a combination thereof. In specific embodiments, the keratolytic agent is benzoyl peroxide, coal tar, dithranol, salicylic acid, selenium disulfide, alpha-hydroxy acid, urea, lactic acid, sodium thioglycolate, zinc pyrithione, or zinc L-pyrrolidone carboxylate.

In various embodiments, therapies provided herein comprise the administration of a composition to the eye of an individual, or to surrounding tissue thereof (e.g., eyelid (e.g., eyelid margin)). Typically, for the purposes of the embodiments described herein, the eye of an individual comprises an ocular component (i.e., the eye globe or "eyeball") and a palpebra component (e.g., comprising an upper lid and a lower lid). In certain instances, the upper and lower lids each generally comprise a palpebra conjunctiva, the palpebra conjunctiva being a tissue that lines the inside of the lid (or at least a portion thereof). In some embodiments, therapies provided herein comprise the administration of a composition to an eyelid margin of an individual. In some embodiments, therapies provided herein comprise the administration of a composition to a single eye of an individual. In other embodiments, therapies provided herein comprise the administration of a composition to two eyes of an individual.

In some instances, the lid-wiper region is a thickened epithelial "lip" that has a conjunctival mucosal morphology that extends from the tarsal conjunctiva up to the crest of the posterior lid border and helps to distribute the precorneal tear film. In certain instances, the lid wiper is the primary part of the lid that interacts with the CL surface and is thus subjected to mechanical friction during the blink, indicating its importance during lens wear. Thus, it is of obvious importance during lens wear. In general, the line of Marx extends from the crest of the posterior lid border and is seen at the bottom of the tear meniscus. A thin band of stainable epithelial cells directly behind the mucocutaneous junction is the basis for Marx's line. Previously, the line of Marx was thought to be the zone in touch with the globe and to represent the wiping surface of the lid border.

In various embodiments discussed herein, administration of an active agent or composition described herein is achieved by administration thereof to the eye or surrounding tissue, such as the eyelid, of an individual in need thereof. In certain embodiments, topical administration to the eye of the individual comprises topical ocular administration, (e.g., topical) palpebra (lid) administration (e.g., to the inside and/or outside of the lid), or a combination thereof. In certain preferred embodiments, (e.g., direct) administration is (e.g., topical) administration to an inner lid surface. In more preferred embodiments, administration is or comprises (e.g., direct) administration to the lid wiper region of the inner lid surface. In certain embodiments, administration is or comprises (e.g., direct) administration to the lid wiper region and the stratified squamous epithelium region and/or the subtarsal fold region of the lid. In some embodiments, administration is or comprises (e.g., direct) administration to the lid wiper region, the stratified squamous epithelium region and the subtarsal fold region of the lid. In certain embodiments, administration is or comprises (e.g., direct) administration to the lid wiper, the stratified squamous epithelium, the subtarsal fold, and the stratified columnar epithelium regions of the lid. In other various embodiments, administration to the meibomian gland orifice of the lid does not also occur.

FIG. 1 illustrates a schematic of a portion of an exemplary eye surface and lid. As illustrated in the figure, at the end of the lid, eye lashes can be observed. Moving inward from the lashes, the inner surface of the lid comprises a stratified squamous epithelium region located proximal to the lashes. Further along the inner surface of the lid, the stratified squamous epithelium leads into the lid wiper region, which is the region of the inner surface that comes into contact with the ocular surface (or contact lens) (e.g., in a normally functioning eyelid). In some instances, when an individual is suffering from contact lens discomfort (CLD) or lid wiper epitheliopathy (LWE), other portions of the inner surface of the lid may also come into contact with the ocular surface. Moving from the lid wiper region (e.g., moving along the inner surface of the lid in a direction distal to the lashes), the inner surface of the lid comprises a subtarsal fold region and a stratified columnar epithelium region. In some instances, a palpebra conjunctiva extends over all or a portion of the inner surface of the lid, such as having a leading edge in the lid wiper region.

The keratolytic and keratoplastic agents described herein are useful in either as an acute therapy (e.g., by a trained specialist or physician) or as a chronic therapy (e.g., in the hands of a patient or caregiver, or alternatively, by a trained specialist or physician). The agents are tested, in certain embodiments, using the assays and methods described herein (e.g., as described in the examples).

One embodiment provides a method for treating CLD or LWE in a patient in need thereof comprising topical administration of a composition comprising a keratolytic agent or keratoplastic agent. In some embodiments, the keratolytic agent is chosen from allantoin, benzoyl peroxide, inorganic selenium compounds such as selenium disulfide, $SeCl_4$, $Na_2SeO_3$, organo-selenium compounds such as Ebselen (2-phenyl-1, 2-benzisoselenazol-3(2H)-one) or its analogues, coal tar, dithranol, salicylic acid, selenium disulfide, alpha-hydroxy acid, urea, lactic acid, sodium thioglycolate, zinc pyrithione, or zinc L-pyrrolodione carboxylate. In some embodiments, the keratolytic agent is selected from the group consisting of benzoyl peroxide, coal tar, dithranol, salicylic acid, selenium disulfide, alpha-hydroxy acid, urea, lactic acid, boric acid, retinoic acid, sodium thioglycolate, allantoin, zinc pyrithione, zinc L-pyrrolidone carboxylate, seleocysteine, selenomethionine, captopril, zofenopril, tiopronin, penicillamine, L-cysteine, gluthatione, dithiothreitol, thiorphan, cysteamine, bucillamine, dimercaprol, 1,1-ethanedithiol, dimercaptosuccinic acid, furan-2-ylmethanethiol, omapatrilat, ovothiol A, rentiapril, thiosalicylic acid, tixocortol, mycothiol, coenzyme A, coenzyme B, disulfiram, psammaplin A, dixanthogen, pantethine, fursultiamine, octotiamine, sulbutiamine, prosultiamine, thiram, lipoic acid, lenthionine, ajoene, allicin, gemopatrilat, thioethanol, thiophospholipid, thiocholesterol, 12-mercaptododecanoic acid, 23-(9-mercaptononyl)-3,6,9,12,15,18,21-heptaoxatricosanoic acid, and sulfanegen. In some embodiments, the keratolytic agent is selenium disulfide. In some embodiments, the keratolytic agent is salicylic acid. In some embodiments the keratolytic agent is not retinoic acid.

In certain embodiments, it is desired that the agents have minimal undesired side effects, such as causing inflammation or other adverse ocular symptoms.

In certain embodiments, a mild or weak keratolytic and/or keratoplastic agents is used in the methods and formulations described herein, e.g., with subjects that produce low levels of keratin. Such mild or weak keratolytic and/or keratoplastic agents are optionally used in a maintenance therapy setting. Mild or weak keratolytic and/or keratoplastic agents include lower concentrations of active keratolytic and/or keratoplastic agents, as well as keratolytic and/or keratoplastic agents that have low inherent activity (as determined, e.g., by the methods described herein). In certain embodiments, the mild or weak keratolytic and/or keratoplastic agents is not boric acid.

In certain embodiments, the composition comprises a therapeutically-effective amount of at least one keratolytic agent (e.g., as described herein) in an ophthalmically-acceptable carrier. In one embodiment, the keratolytic agent is benzoyl peroxide. In another embodiment, the keratolytic agent is coal tar. In another embodiment, the keratolytic agent is dithranol. In another embodiment, the keratolytic agent is salicylic acid. In another embodiment, the keratolytic agent is selenium sulfide (e.g., selenium disulfide). As used herein, the terms "selenium sulfide" and "selenium disulfide" are used interchangeably to refer to the chemical compound having the formula $SeS_2$ where the ratio of selenium to sulfur is approximately 1:2. In another embodiment, the keratolytic agent is zinc pyrithione. In another embodiment, the keratolytic agent is zinc L-pyrrolidone carboxylate.

In some embodiments, more than one keratolytic agent is used.

In some embodiments, administration of a keratolytic agent to a keratin obstruction results in proteolysis of desmosomes forming tight junctions between keratinocytes.

In some embodiments, administration of a keratolytic agent results in lysis, including the hydrolysis of disulfide bonds. In some embodiments, administration of a keratolytic agent reduces the production of keratin.

In specific embodiments, the keratolytic agent comprises benzoyl peroxide. In some embodiments, the composition comprises about 2.5%, about 5%, or about 10% benzoyl peroxide (e.g., weight/weight percent of the total composition). In some embodiments, the composition comprises at least about 2.5%, about 5%, about 10%, or more benzoyl peroxide. In some embodiments, the composition comprising benzoyl peroxide is a suspension, emulsion, cream, lotion, gel (e.g., aqueous or non-aqueous), or ointment. In some embodiments, the composition comprising benzoyl peroxide is applied as a thin layer to clean skin initially once daily on alternate days, and is then gradually increased up to twice daily as tolerance develops.

In certain specific embodiments, the keratolytic agent is coal tar. In some embodiments, the composition comprises an about 5% to about 10% solution of coal tar. In some embodiments, the composition comprising coal tar is at least about 5%, about 6%, about 7%, about 8%, about 9%, about 10%, or greater solution of coal tar. In one embodiment, the composition comprising coal tar is an about 1% ointment of crude coal tar. In some embodiments, the coal tar inhibits excessive proliferation of epidermal cells by reducing DNA synthesis and mitotic activity to normal levels.

In some specific embodiments, the keratolytic agent is dithranol. In some embodiments, the composition comprises an about 0.1% to about 2.0% ointment of dithranol. In some embodiments, the composition comprising dithranol is at least about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, or greater of dithranol. In some embodiments, the composition comprising dithranol is started as an about 0.1% ointment. After one or more days, such as after 7 days, the concentration may be increased to about 0.25% and subsequently increased (e.g., doubled), if necessary, at intervals (e.g., weekly intervals) to a maximum strength (e.g., about 2%). In some embodiments, a thin layer of ointment is applied once daily to the affected areas for one or more weeks, such as 2-4 weeks. In some embodiments, the ointment is left in place for about 10 to about 20 minutes before the area is rinsed thoroughly. In some embodiments, the dithranol slows epidermal cell division and inhibits excessive proliferation and keratinization of epidermal cells in patients.

In certain specific embodiments, the keratolytic agent is salicylic acid. In some embodiments, the composition comprises between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein) salicylic acid. In some embodiments, the composition comprises about 0.1% to about 6% salicylic acid. In some embodiments, the composition comprises at least about 0.1%, about 1%, about 2%, about 3%, about 4%, about 5%, about 6%, or greater salicylic acid. In some embodiments, the concentration of the salicylic acid in the composition is at least about 0.01%, such as at least about 0.05%, about 0.1%, about 1%, about 2%, about 2.5%, about 5%, about 10%, or more. In some embodiments, the concentration of the salicylic acid in the composition is no more than about 10%, such as no more than about 5%, about 2.5%, about 2%, about 1%, about 0.5%, about 0.1%, or less. In some embodiments, the composition comprises between about 0.01% to about 30% salicylic acid, such as about 0.01% to about 10%, about 0.1% to about 10%, or about 0.1% to about 30% salicylic acid. In some embodiments, the composition comprising salicylic acid is an ointment or paste. In some embodiments, the composition comprising salicylic acid is applied initially as a thin layer of about 2% ointment or paste, and is applied daily. In some embodiments, the concentration is gradually increased to a maximum concentration of about 5%, and treatment is continued for as long as necessary.

In some specific embodiments, the keratolytic agent is selenium disulfide. In some embodiments, the composition comprises between about 0.01% to about 30% (e.g., about 0.01% to about 10%, about 0.01% to about 5%, about 0.01% to about 2.5%, about 0.01% to about 1%, about 0.1% to about 10%, about 0.1% to about 5%, about 0.1% to about 2.5%, about 0.1% to about 1%, or any useful range therein) selenium disulfide. In some embodiments, the composition comprises about 0.01% to about 10% selenium disulfide. In some embodiments, the composition comprises at least about 0.01%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, or greater selenium disulfide. In some embodiments, the concentration of the selenium disulfide in the composition is at least about 0.01%, such as at least about 0.05%, about 0.1%, about 1%, about 2%, about 2.5%, about 5%, about 10%, or more. In some embodiments, the concentration of the selenium disulfide in the composition is no more than about 10%, such as no more than about 5%, about 2.5%, about 2%, about 1%, about 0.5%, about 0.1%, or less. In some embodiments, the composition comprises between about 0.01% to about 30% selenium disulfide, such as about 0.01% to about 10%, about 0.1% to about 10%, or about 0.1% to about 30% selenium disulfide. In some embodiments, the composition comprising selenium disulfide is a suspension, emulsion, cream, lotion, gel (e.g., aqueous or non-aqueous), or ointment. In some embodiments, the composition comprising selenium disulfide is a semi-solid composition. In some embodiments, the composition comprising selenium disulfide is a lotion. In some embodiments, the composition comprising selenium disulfide is a cream. In some embodiments, the composition comprising selenium disulfide is an ointment. In some embodiments, the composition comprising selenium disulfide is a suspension. In some embodiments, the composition comprising selenium disulfide is a dispersion. In some embodiments, the composition comprising selenium disulfide is a solution. In other embodiments, the composition is a suspension, hydrophobic oil, foam, liposome, emulsion, lotion, microparticle, or other suitable formulation.

In some embodiments, the composition comprises inorganic selenium compounds that are inhibitors of prostaglandin synthase, the enzyme involved in the production of prostaglandins. The selenium compounds demonstrating this inhibitory effect include $SeCl_4$ and $Na_2SeO_3$. It is known that the proinflamatory action of prostaglandins enhances keratinization and therefore these water-soluble inorganic selenium compounds that interfere with the production of prostaglandin may be useful in reducing keratinization.

In some embodiments, the composition comprises organo-selenium compounds. Organo-selenium compounds such as Ebselen are antioxidant and anti-inflammatory agents inhibiting cyclooxygenase and lipooxygenase enzymes and acting as scavenger of hydrogen peroxide as well as hydroperoxides including membrane bound phospholipid and cholesterylester hydroperoxides. Anti-inflammatory agents are known to inhibit keratinization and therefore ebselen and other organo-selenium analogues may act as keratolytic agents through this antioxidant/anti-inflammatory activity.

In some embodiments, the formulation comprising the keratolytic and/or keratoplastic agent further includes an additional therapeutic agent that is not a meibomian gland opening pharmacological agent. In some embodiments the formulation does not contain jojoba wax or jojoba extract. In some embodiments the formulation does not include boric acid. In some embodiments, the formulation does not include retinoic acid. Alternatively, in some embodiments, the formulation with the keratolytic and/or keratoplastic agent excludes any additional therapeutic agent, other than an optional additional meibomian gland opening pharmacological agent.

In certain embodiments, a composition comprises (e.g., further comprises) a local anesthetic. In some embodiments, the local anesthetic chosen from an aminoamide local anesthetic, or an aminoester local anesthetic.

The term "local anesthetic" as used herein refers to an agent that induces a reversible absence of pain sensation. In some embodiments, a local anesthetic may also induce temporary muscle paralysis in addition to inducing a reversible absence of pain sensation.

The local anesthetic agents described herein are useful primarily as an acute therapy, e.g., under the guidance of a physician or other trained specialist. The agents are tested, in certain embodiments, using the assays and methods described herein.

In some embodiments, the local anesthetic is an aminoamide. In some embodiments, the local anesthetic is an aminoester. In some embodiments, the local anesthetic comprises a combination of two or more local anesthetics. In some embodiments, the combination comprises an aminoamide local anesthetic and an aminoester local anesthetic.

In some embodiments, the local anesthetic is an aminoester selected from the group consisting of: benzocaine, chloroprocaine, cocaine, cyclomethycaine, dimethocaine, larocaine, piperocaine, propoxycaine, procaine, novocaine, proparacaine, tetracaine, and amethocaine.

In some embodiments, the local anesthetic is an aminoamide selected from the group consisting of: articaine, bupivacaine, cinchocaine, dibucaine, etidocaine, levobupivacaine, lidocaine, lignocaine, mepivacaine, prilocaine, ropivacaine, and trimecaine.

In some embodiments, the local anesthetic is a combination of lidocaine and prilocaine or a combination of lidocaine and tetracaine.

In some embodiments, the local anesthetic is a naturally derived local anesthetic. In some embodiments, the naturally derived local anesthetic is selected from the group consisting of: saxitoxin, neosaxitoxin, tetrodotoxin, menthol, eugenol, and cocaine.

In some embodiments, the local anesthetic is mixed with a vasoconstrictor to increase the duration of the local anesthesia by constricting blood vessels. In some embodiments, priolocaine hydrochloride is mixed with epinephrine. In some embodiments, lidocaine, bupivacaine are mixed with epinephrine. In some embodiments, iontocaine is mixed with lidocaine and epinephrine. In some embodiments, septocaine is mixed with a combination of articaine and epinephrine. In some embodiments, local anesthetic, bupivacaine or lidocaine are mixed in combination with a steroid.

In some embodiments, the (e.g., topical) compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in Remington: The Science and Practice of Pharmacy (Gennaro, 21$^{st}$ Ed. Mack Pub. Co., Easton, Pa. (2005)). Other additives, such as a preservative is optionally provided.

In certain embodiments, compositions provided herein comprise any suitable additional agent or additive. In specific embodiments, additives are included, such as to improve performance and/or efficacy of a composition or formulation provided herein. In some instances, for example, a composition provided herein comprises a penetration enhance and/or surfactant (e.g., ionic, anionic, cationic, non-ionic, lipid (e.g., oleic or caprylic), BNZ, or the like). In some instances, a composition provided herein comprises an excipient that otherwise improves drug penetration and/or functions to solubilize plaque or keratinization, such as present on an eyelid or lens, such as according to a process described herein.

In certain specific embodiments, the pharmaceutically acceptable composition consists essentially of the at least one keratolytic agent (e.g., as described herein) and the ophthalmically-acceptable carrier. In certain specific embodiments, the pharmaceutically acceptable composition consists of the at least one keratolytic agent (e.g., as described herein) and the ophthalmically-acceptable carrier.

Described herein are methods for treating various ocular disorders (e.g., LWE and/or CLD) in an individual (e.g., patient) in need comprising topical administration of a composition described herein to an individual (e.g., patient) (e.g., to the inner surface of one or more eyelid thereof) in need thereof. In some embodiments, the individual is a patient, such as a patient under medical care (e.g., for an ocular condition and/or another condition). In some instances, such therapies constitute acute therapy, such as wherein, in some embodiments, a stronger pharmacological agent (either in terms of concentration of the agent or the inherent activity of the agent) is utilized. A maintenance use, in one embodiment, allows for the use of lower concentrations of the agent, or agents with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider, such as a caregiver. In some embodiments, the patient applies the pharmacological agent (e.g., a composition comprising a keratolytic agent) him/herself (e.g., to the inner surface of one or more eyelid thereof). In one embodiment, such administration occurs over an extended period of time; one way of describing this patient-administered multi-administration mode is as a chronic use. In general, different or second formulations of the pharmacological agent are recommended for chronic or patient-administered uses. In one embodiment the different or second formulation utilizes a lower concentration of the pharmacological agent. In another embodiment, the second or different formulation utilizes a pharmacological agent that has a lower activity than the first formulation.

In some embodiments, the topical administration of the composition comprising a therapeutically-effective amount of at least one keratolytic agent in an ophthalmically-acceptable carrier occurs until the (e.g., abnormal) keratinization (e.g., parakeratinization (pk)) is reduced. In some embodiments, the topical administration of the composition comprising a therapeutically-effective amount of at least one keratolytic agent in an ophthalmically-acceptable carrier occurs periodically after keratinization reduction is achieved. In some embodiments, the topical administration of the composition comprising a therapeutically-effective amount of at least one keratolytic agent in an ophthalmically-acceptable carrier is a single administration. In some embodiments, the topical administration of the composition comprising a therapeutically-effective amount of at least one keratolytic agent in an ophthalmically-acceptable carrier is a periodic administration. In some embodiments, the topical administration of the composition comprising a therapeutically-effective amount of at least one keratolytic agent in an ophthalmically-acceptable carrier occurs once per day. In some embodiments, the topical administration of the composition comprising a therapeutically-effective amount of at least one keratolytic agent in an ophthalmically-acceptable carrier occurs twice per day. In some embodiments, the topical administration of the composition comprising a therapeutically-effective amount of at least one keratolytic agent in an ophthalmically-acceptable carrier occurs twice per week.

In some embodiments, the composition for topical administration, comprising a therapeutically-effective amount of at least one keratolytic agent in an ophthalmically-acceptable carrier is a semi-solid composition. In some embodiments, the composition for topical administration, comprising a therapeutically-effective amount of at least one keratolytic agent in an ophthalmically-acceptable carrier is homogenous. In some embodiments, the composition for topical administration, comprising a therapeutically-effective amount of at least one keratolytic agent in an ophthalmically-acceptable carrier is a dispersion. In some embodiments, the composition for topical administration, comprising a therapeutically-effective amount of at least one keratolytic agent in an ophthalmically-acceptable carrier is hydrophilic. In some embodiments, the composition for topical administration, comprising a therapeutically-effective amount of at least one keratolytic agent in an ophthalmically-acceptable carrier has an oleaginous base. In some embodiments, the composition for topical administration, comprising a therapeutically-effective amount of at least one keratolytic agent in an ophthalmically-acceptable carrier has at least one ophthalmically-acceptable excipient. In certain embodiments, the composition for topical administration is a gel, such as a non-aqueous gel.

In certain preferred embodiments, a semi-sold or other viscous formulation is utilized (e.g., a gel (e.g., gel emulsion suspension foam), cream or ointment, or other formulation, such as a suspension, hydrophobic oil, foam, liposome, emulsion, lotion, microparticle, or the like). In some instances, such formulations facilitate maintaining the pharmacologically active formulation at or near the site to be treated (e.g., the site of dysfunction, such as trauma, abnormal keratinization, or the like). In some instances, a semi-solid or other viscous formulation does little migration from the administration site.

In some embodiments, the topical administration of the composition comprising a pharmacological agent occurs once per week. In some embodiments, the topical administration of the composition comprising a pharmacological agent occurs twice per week. In some embodiments, the topical administration of the composition comprising a pharmacological agent occurs every other day. In some embodiments, the topical administration of the composition comprising a pharmacological agent occurs every day. In some embodiments, the topical administration of the composition comprising a pharmacological agent occurs several times per day.

In some embodiment, the method comprises treatment in an acute treatment scenario. In another embodiment, the method comprises treatment of a patient naïve to treatment. In another embodiment, the method comprises treatment in a chronic treatment scenario. In another embodiment, the method comprises treatment in a maintenance therapy scenario. In an acute treatment scenario, the administered dosage of pharmacological agent may be higher than the administered dosage of pharmacological agent employed in a chronic treatment scenario or a maintenance therapy scenario. In an acute treatment scenario, the pharmacological agent maybe different from the pharmacological agent employed in a chronic treatment scenario. In some embodiments, the course of therapy begins in the initial phase of therapy as an acute treatment scenario and later transitions into a chronic treatment scenario or a maintenance therapy scenario. In some embodiments, the pharmacological agent administered in the acute treatment scenario is a local anesthetic, and the pharmacological agent administered in the chronic treatment scenario or a maintenance therapy scenario is a keratolytic agent and/or keratoplastic agent. In some embodiments, the pharmacological agent administered in the acute treatment scenario is a keratolytic agent and/or keratoplastic agent, and the pharmacological agent administered in the chronic treatment scenario or a maintenance therapy scenario is a keratolytic agent and/or keratoplastic agent.

In certain clinical presentations, patients may require an initial treatment administered by a physician or healthcare professional, either by placing a more highly concentrated formulation of one of the therapeutic agents described herein. In the event the higher concentration formulations are required, the application thereof may require ocular shielding or other activity to minimize the impact of irritation or disruption of the ocular surface or surrounding tissues. Following such a procedure, a patient may be given a different formulation of active agent to take home to apply periodically to the inner surface of the lid. Such application may occur twice daily, once per day, weekly, twice per week, biweekly, or monthly, depending on the formulation activity and the desired product profile of the therapy.

In some embodiments, a method provided herein provides improvements in one or more symptoms of CLD and/or LWE, such as dryness, grittiness, scratchiness, soreness, irritation, burning, or watering. In some embodiments, improvements in such symptoms can be evaluated according to a subjective vision assessment (e.g., VAS) or another subjective scoring system (e.g., CLDEQ-8). In some embodiments, a method provided herein provides improvements in eyelid signs of CLD. In some embodiments, a method provided herein provides improvements in the tear film signs of CLD. In some embodiments, a method provides improvements in the CLDEQ-8 measurement tool. In some embodiments, a method provides improvements in comfortable wear time (e.g., for contact lenses). In some embodiments, a method provides improvements in subjective vision assessment (e.g., as assessed by a visual analogue scale, VAS). In some embodiments, an improvement in one or more symptoms of CLD and/or LWE, including comfortable wear time, is observed within about one month of administration of a composition (e.g., according to a method provided herein), such as within about four weeks, three weeks, two weeks, one week, three days, two days, or sooner. In some embodiments, an improvement in one or more symptoms of CLD and/or LWE, including comfortable wear time, is observed within about two months of administration of a composition (e.g., according to a method provided herein). In some embodiments, improvement in a symptom of CLD and/or LWE continues over a period of administration, such as over one week, two weeks, three weeks, four weeks, one month, two months, or longer.

In some embodiments, the individual (e.g., patient) being treated according to a method described herein wears one or more contact lenses (e.g., on a regular basis, such as for one or more hours per day or one or more days per week). In some embodiments, the individual being treated according to a method described herein wears one or more contact lenses two or more days per week, such as three, four, five, six, or seven days per week. In some embodiments, the individual being treated according to a method described herein wears one or more contact lenses for the duration of treatment (e.g., as described herein). In other embodiments, the individual being treated according to a method described herein does not wear one or more contact lenses for the duration of treatment (e.g., regular wear is resumed following a prescribed treatment course). In some embodiments, the individual wears soft contact lenses. In some embodiments, the individual wears hard contact lenses (e.g., rigid gas permeable contact lenses). In some embodiments, the individual wears disposable contact lenses (e.g., contact lenses configured to be worn a single time, such as over the course of a single day) or extended wear contact lenses (e.g., contact lenses configured to be worn for more than one day, such as contact lenses configured to be worn for more than one week, more than two weeks, more than three weeks, or more than four weeks). In some embodiments, the individual wears orthokeratology (ortho-K) lenses. In some embodiments, the individual wears decorative or cosmetic contact lenses, such as colored contact lenses.

In some embodiments, improvements in one or more symptoms of CLD and/or LWE can be evaluated according to the 8-item Contact Lens Dry Eye Questionnaire (CLDEQ-8). The CLDEQ-8 is an 8-item questionnaire that queries the frequency and late-day intensity of discomfort, dryness, and changeable, blurry vision and the frequency of closing eyes for a relief while wearing contact lenses and removal of lenses earlier than planned for relief of symptoms. The CLDEQ-8 is optionally self-administered. A CLDEQ-8 score of ≥12 points can identify contact lens (e.g., soft contact lens) wearers who could benefit from clinical management of their contact lens-related symptoms. A clinically important difference for the CLDEQ-8 is defined as ±3 points (see Chalmers et al. *Cont. Lens. Anterior Eye.* 2016 October; 39(5):342-52).

In some embodiments, a method provided herein further comprises one or more additional therapeutic interventions such as application of a warm compress, debridement, and/or therapeutic expression (e.g., manual expression or physical expression using an instrument such as LipiFlow). In some embodiments, a method provided herein further comprises performing debridement or debridement coupled with therapeutic expression in an eye of an individual. In some embodiments, debridement is performed in one eye and debridement coupled with therapeutic expression is performed in another eye. In some embodiments, a therapeutic intervention (also referred to herein as a physical intervention) is performed after administration of a composition provided herein. For example, in some embodiments, the physical intervention is performed at least about 5 minutes after administration of the composition, such as at least about 10 minutes, about 20 minutes, about 30 minutes, about 1 hour, about 2, hours, about 4 hours, about 8 hours, about 12 hours, about 24 hours, about 48 hours, about 72 hours, about 1 week, about 2 weeks, about 3 weeks, about 4 weeks, about 1 month, or longer after administration of a composition provided herein. In some embodiments, the composition is administered periodically and the physical intervention is performed a single time, such as about 1 month after an initial administration of the composition.

One aspect of the methods of treatment described herein is the location of the topical administration of the composition. In one embodiment, the composition comprising a pharmacological agent is administered such that little or no irritation to eye or its surrounding tissue occurs. In one embodiment, the composition comprising a pharmacological agent (e.g., keratolytic agent) is administered to an inner surface of an eyelid of an individual in need thereof (e.g., one or both upper lid and/or one or both lower lid).

One additional embodiment of the methods of treatment described herein is the use of a protective element provided to the eye to avoid irritation to the eye. Although the formulations described herein are generally non-irritating, in some embodiments (e.g., high concentration of agent or when used on a sensitive eye) a protective element provides an additional layer of safety and comfort for the patient. In one embodiment, the composition comprising a pharmacological agent is administered while an eye shield is placed on the eye to reduce contact of the pharmacological agent with the cornea and/or conjunctiva such that reduced irritation to eye occurs. In some embodiments, the eye shield is a contact lens or an eye covering. In some embodiments, the eye covering comprises a self-adhesive. In one embodiment, the composition comprising a pharmacological agent is administered while the lid is pulled away from the globe to reduce contact of the pharmacological agent with the cornea and/or conjunctiva such that reduced irritation to eye occurs.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms of a disorder described herein, such as CLD and/or LWE, in either a chronic or acute therapeutic scenario. In one embodiment, treatment includes a reduction of a terminal duct obstruction.

The term "recurrence," or "reducing relapse" symptoms of a disorder described herein, such as CLD and/or LWE, in a chronic therapeutic scenario.

The term "keratolytic agent" and/or "keratoplastic agent" as used herein refers to an agent that softens, disrupts, dissolves, solubilizes, or loosens a keratinized obstruction, or prevents the formation of a keratinized obstruction. Specifically, the term "Keratolytic agents" refers to agents used to promote softening and dissolution of keratin and the term "keratoplastic agents" refers to agents used to reduce keratin production.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are not dissolved, but can get suspended throughout at least a portion of the bulk of the solvent.

Concentrations of agents provided herein are based on any suitable measurement, such as wt. %, w/w %, or w/v %.

The term "about" means any acceptable amount, such as suitable to achieve the stated purpose. In some instances, "about" refers to, for example, plus or minus 20%, or plus or minus 10%, or plus or minus 5%.

The term "comprising," as used herein, also includes an explicit disclosure of "consisting of" and "consisting essentially of."

EXAMPLES

Example 1: Pharmacological Active Formulations

High viscosity formulations are prepared, such as for administration according to the disclosures provided herein. Any suitable formulation, such as a cream, ointment, emulsion, suspension, microspheres, or the like are optionally utilized. In various embodiments, exemplary ophthalmic ointment formulations are prepared according to the following formulations:

| Ingredient | % weight/volume |
|---|---|
| Water | 3% |
| 80% White Petrolatum | 90% |
| 20% Mineral Oil | 3% |
| Liquid Lanolin | 3% |

| Ingredient | % weight/volume |
|---|---|
| Salicylic acid | 1% |
| Water | 3% |
| 80% White Petrolatum | 90.9% |
| 20% Mineral Oil | 3% |
| Liquid Lanolin | 3% |
| Salicylic acid | 0.1% |
| Water | 3% |
| 80% White Petrolatum | 90% |
| 20% Mineral Oil | 3% |
| Liquid Lanolin | 3% |
| Selenium disulfide | 1% |
| Water | 3% |
| 80% White Petrolatum | 90.9% |
| 20% Mineral Oil | 3% |
| Liquid Lanolin | 3% |
| Selenium disulfide | 0.1% |

Other formulations, such as ointment/semi-solid, surfactant formulations are contemplated and provided herein.

Abnormal keratitis is induced in the eyes of rabbits using a 0.5% benzalkonium chloride solution. Each rabbit is assigned to receive an ointment provided herein in one eye and a control ointment in the other eye. Evaluation of the inner surface of the lid, such as in the lid wiper and/or conjunctival folds is evaluated.

Example 2: Diagnosis and Treatment

An individual is admitted in a clinical setting after having worn his soft contacts daily for at least 6 months prior to the office visit. The individual is asked to score satisfaction in the overall comfort of his contact lenses and contact lens wear time. The individual is also assessed based on one or more symptom scoring metrics. In some instances, the Standard Patient Evaluation of Eye Dryness (SPEED) questionnaire is provided to the individual (e.g., and scored out of a possible 28 points). In certain instances, the Contact Lens Dry Eye Questionnaire-8 (CLDEQ-8) is also provided to the individual and scored (e.g., out of 35 possible points) (see, e.g., Chalmers et al. Invest. Ophth. & Visual Science, April 2009, 50: 6337). In certain instances, the individual is (e.g., also) assessed using common symptoms for contact lens discomfort such as dryness, grittiness, soreness or burning.

The individual's eyes are evaluated for appearance. The eyelashes are also evaluated for appearance (e.g., signs of symptoms), such as checking for madarosis, blepharitis, seborrheic scurf, or collarettes. Fluorescein tear break-up time is analyzed in each eye, such as measured using Dry Eye Test (DET) Strips by Amcon.

In some instances, direct evaluation of the lid wiper region is performed. For example, in some instances a 40-μL drop of 2% fluorescein diluted from a test strip (Fluor-I-strip A.T. ophthalmic strips 1 mg; Wyeth-Ayerst Laboratories, Rouses Point, N.Y.) with unpreserved saline solution (AstraZeneca) by soaking for 1 minute was instilled into the lower conjunctival sac of each eye. After 1 minute, a 40-μL drop of lissamine green dye is prepared by soaking a strip (OpGreen 1.5 mg; Ophtechnics Unlimited, Haryana, India) in unpreserved saline solution for 1 minute and is also applied to each eye. One minute after the last instillation of dye the eye is examined for changes in the lid wiper region. Evaluation of the lid wiper region, such as for increases in the sagittal width and horizontal length of lissamine green staining and/or an increase in lid-parallel conjunctival folds. Changes in meibomian gland functional changes may also be evaluated, though such dysfunction is not necessary to identify CLD or LWE.

In certain instances, depending on the scoring of the symptom score questionnaires and/or analysis of the LWE, a determination of pre-symptomatic CLD or LWE is determined. In other instances, depending on the scoring of the symptom score questionnaires and/or analysis of the LWE, a determination of mild CLD or LWE is determined. In still other instances, depending on the scoring of the symptom score questionnaires and/or analysis of the LWE, a determination of mild CLD or LWE is determined.

For example, in the instance where an individual scores a 4 out of 28 on the SPEED questionnaire, a 6 out of 35 on the CLDEQ-8 questionnaire, has no particular problem with common symptoms for contact lens discomfort such as dryness, grittiness, soreness or burning, has eyes that appear white and quiet, has eyelashes that are normal without madarosis, blepharitis, seborrheic scurf, or collarettes, has a fluorescein tear break-up time was 4-6 s as measured using Dry Eye Test (DET) Strips by Amcon, has no signs of meibomian gland abnormality, has increases in the sagittal width and horizontal length of lissamine green staining and an increase in lid-parallel conjunctival folds is diagnosed as pre-symptomatic Contact Lens Discomfort (CLD). Thus, despite the lack of "symptoms" of CLD, the patient is diagnosed with (pre-symptomatic) CLD based primarily on the signs of CLD.

However, in the instances where an individual scores a 11 out of 28 on the SPEED questionnaire, a 15 out of 35 on the CLDEQ-8 questionnaire, suffers from stinging, foreign body sensation, tearing and dry eye, has eyes that appear white and quiet, has eyelashes that are normal without madarosis, blepharitis, seborrheic scurf, or collarettes, has a fluorescein tear break-up time was 11-12 seconds as measured using Dry Eye Test (DET) Strips by Amcon, has no signs of meibomian gland abnormality, has no signs of conjunctival staining staining is diagnosed as symptomatic Contact Lens Discomfort (CLD). Thus, despite the lack of "signs" of CLD, the patient is diagnosed with CLD based on symptoms alone.

A composition described herein, such as in Example 1, is administered to the inner surface of an eyelid identified as being pre-symptomatic or symptomatic for CLD (or LWE). After administration (e.g., single and/or multiple administration), the evaluation (e.g., symptoms and signs) described herein is re-administered to determine improvement in condition.

Figure 4:
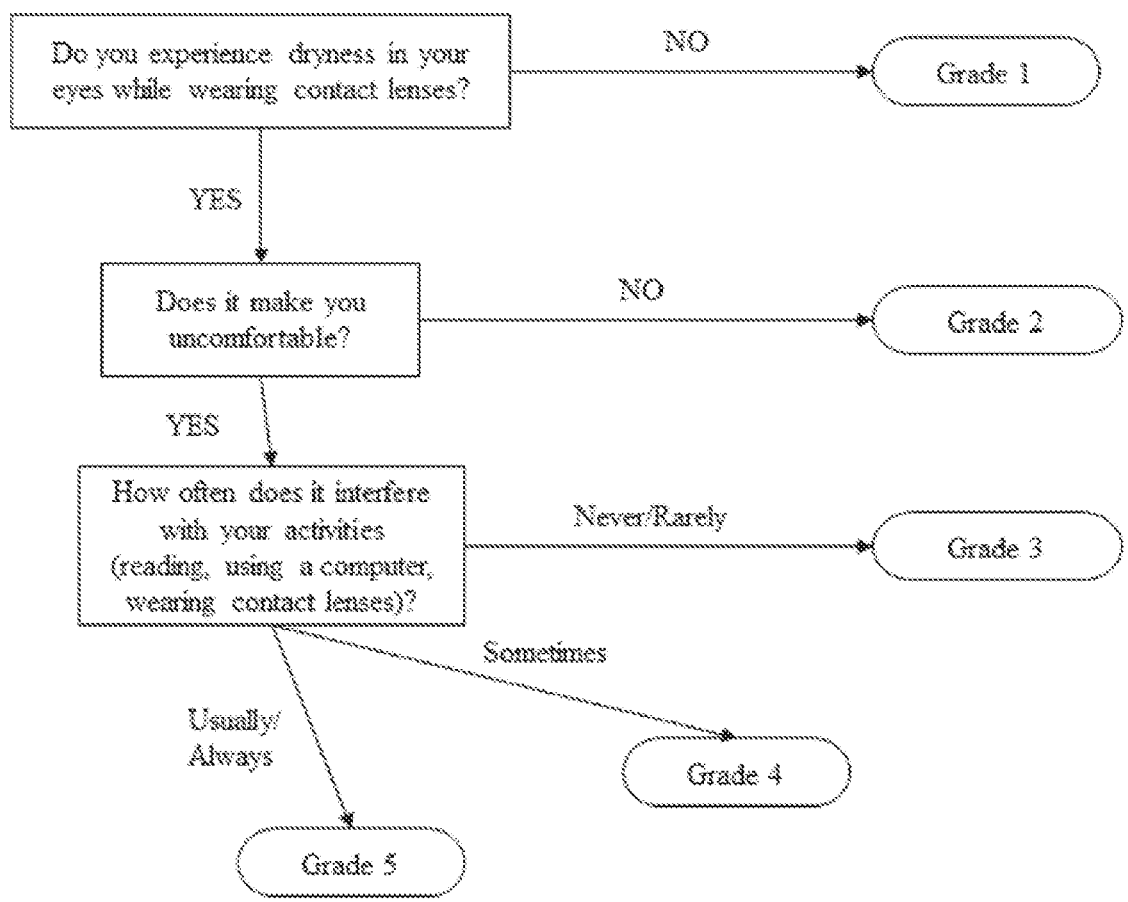
FIG. 4 shows the Berkeley Dry Eye Flow Chart (DEFC).

Example 3: Clinical Evaluation of CLD Treatment 6 patients with CLD were treated with a drug formulation comprising 1% selenium disulfide. Treatment consisted of twice a week application of the drug product on the lower eyelid of both eyes. Patients were followed up at the clinic at 14 days and 4 weeks and their discomfort levels were assessed with Visual Analog Scale (VAS) and Contact Lens Dry Eye Questionnaire-8 (CLDEQ-8) questionnaires (4 weeks only). FIGS. 2-4 illustrate mechanisms for evaluating the efficacy of the treatment, including the VAS, the CLDEQ-8, and the Berkeley Dry Eye Flow Chart (DEFC).

Table 1 shows patients' change from baseline in dryness VAS scale.

| Subject ID | Baseline-Day 14 | Baseline-Month 1 |
| --- | --- | --- |
| #201 | 52 | 14 |
| #202 | 22 | 31 |
| #204 | 34 | 70 |
| #205 | 5 | 3 |
| #208 | 26 | 68 |
| #209 | 7 | 15 |
| Mean | 24 | 34 |
| SD | 17.56 | 28.92 |

As shown in Table 1, on average, patients improved 24 points after 14 days of treatment and 34 points after 4 weeks of treatment.

Table 2 shows patients' change from baseline on the CLDEQ-8 questionnaire.

| Subject ID | Baseline Total Score | Week 4 Total Score | Baseline-Week 4 |
| --- | --- | --- | --- |
| #201 | 18 | 16 | 2 |
| #202 | 21 | 16 | 5 |
| #205 | 11 | 12 | −1 |
| #208 | 21 | 13 | 8 |
| #209 | 16 | 15 | 1 |
| Mean | 17 | 14 | 3 |
| SD | 4.16 | 1.81 | 3.53 |

As shown in Table 2, of the five patients with baseline and month 1 data, 80% (4/5) improved on the CLDEQ-8 questionnaire and 40% (2/5) achieved a change from baseline in excess of the clinically important difference (e.g., greater than 3 points change) for the CLDEQ-8 following treatment with the drug formulation. Of the four patients with an abnormal baseline CLDEQ-8 score, 100% (4/4) improved on the CLDEQ-8 and 50% (2/4) achieved a change from baseline in excess of the clinically important difference for the CLDEQ-8 following treatment with the drug formulation. The mean change from baseline to month 1 achieved the clinically important difference for the CLDEQ-8 of ±3 points.

Patients 202 and 208 had baseline scores of 21 on the CLDEQ-8, which is indicative of a patient who could benefit from clinical management of their contact lens-related symptoms. After one month of treatment with the drug formulation, Patient 208 presented with a CLDEQ-8 score of 13, which is indicative of a patient who has significantly improved in their contact-lens related symptoms. Similarly, after one month of treatment with the drug formulation, Patient 202 presented with a CLDEQ-8 score of 16, which is indicative of a patient who has significantly improved in their contact lens-related symptoms. Patient 202's improvement was driven by reductions in how noticeable blurry or foggy vision was at the end of his/her contact lens wearing time and a reduction in how often, during the past 2 weeks, his/her eyes bothered him/her so much while wearing his/her contact lenses that he/she felt as if he/she needed to stop whatever he/she was doing and take out his/her contact lenses. Patient 208's improvement was driven by reductions in eye dryness and discomfort frequency and severity at the end of his/her contact lens wearing time.

Thus, patients report improvements in key symptoms of CLD (e.g., dryness and discomfort) across instruments (e.g., CLDEQ-8 and VAS) and reductions in how noticeable blurry or foggy vision is at the end of their contact lens wearing time when using the drug formulation.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for improving comfortable wear time of a contact lens in an individual in need thereof, the method comprising:
    (i) topically administering to an eye or an eyelid associated with the eye of the individual a pharmaceutically acceptable composition, the composition comprising a therapeutically-effective amount of at least one keratolytic agent and an ophthalmically-acceptable carrier; and
    (ii) wearing a contact lens in the eye, wherein comfortable wear time of the contact lens in the individual is increased relative to the comfortable wear time of the contact lens in the individual in the absence of the topical administration of the composition, and wherein the individual has not been diagnosed with meibomian gland dysfunction (MGD).

2. The method of claim 1, wherein the composition is administered to at least a portion of a palpebra conjunctiva of the eye of the individual.

3. The method of claim 2, wherein the comfortable wear time of the contact lens is associated with an alteration to the palpebra conjunctiva, or a portion thereof.

4. The method of claim 3, wherein the alteration to the palpebra conjunctiva comprises trauma or keratinization of the palpebra conjunctiva, or a portion thereof.

5. The method of claim 1, wherein the composition is administered to an eyelid margin of the eye of the individual.

6. The method of claim 1, wherein the method comprises treating inflammation, dryness, or pain associated with contact lens discomfort.

7. The method of claim 1, wherein the method provides improvements in eyelid signs or tear film signs of contact lens discomfort (CLD).

8. The method of claim 1, wherein the individual suffers from lid wiper epitheliopathy (LWE).

9. The method of claim 8, wherein the eye of the individual comprises a lid wiper region and the pharmaceutical composition is directly administered to and/or reaches at least a portion of the lid wiper region following administration.

10. The method of claim 9, wherein the lid wiper epitheliopathy comprises trauma to the lid wiper region of the eyelid.

11. The method of claim 1, wherein the method provides an improvement in horizontal (width) and/or sagittal (height) lesions and/or in lid parallel conjunctival folds (LIPCOF).

12. The method of claim 1, wherein the at least one keratolytic agent is selected from the group consisting of benzoyl peroxide, coal tar, dithranol, salicylic acid, selenium disulfide, alpha-hydroxy acid, urea, lactic acid, sodium thioglycolate, zinc pyrithione, and zinc L-pyrrolidone carboxy late.

13. The method of claim 12, wherein the at least one keratolytic agent is salicylic acid.

14. The method of claim 12, wherein the at least one keratolytic agent is selenium disulfide.

15. The method of any one of claim 14, wherein the concentration of the at least one keratolytic agent in the composition is between about 0.01% to about 10% by weight.

16. The method of claim 1, wherein the individual has contact lens discomfort (CLD), or symptoms thereof.

17. The method of claim 16, further comprising assessing the symptoms using a symptom scoring technique.

18. The method of claim 17, wherein the symptom scoring technique is suitable for diagnosing contact lens discomfort (CLD), lid wiper epitheliopathy (LWE), eye dryness, eye pain, or eye inflammation.

19. The method of claim 18, wherein the individual has been diagnosed with an ocular disorder using a contact lens dry eye questionnaire (CLDEQ) measurement tool.

20. The method of claim 19, wherein the individual has a CLDEQ-8 score of at least 5.

* * * * *